US011419540B2

(12) United States Patent
Knight et al.

(10) Patent No.: US 11,419,540 B2
(45) Date of Patent: Aug. 23, 2022

(54) DIGITAL IMAGING SYSTEMS AND METHODS OF ANALYZING PIXEL DATA OF AN IMAGE OF A SHAVING STROKE FOR DETERMINING PRESSURE BEING APPLIED TO A USER'S SKIN

(71) Applicant: THE GILLETTE COMPANY LLC, Boston, MA (US)

(72) Inventors: Leigh Knight, Reading (GB); Susan Clare Robinson, Windsor (GB); Sean Patrick Wheeler, Bromley (GB); Kevin David Cowley, Reading (GB)

(73) Assignee: THE GILLETTE COMPANY LLC, Boston, MA (US)

( * ) Notice: Subject to any disclaimer, the term of this patent is extended or adjusted under 35 U.S.C. 154(b) by 182 days.

(21) Appl. No.: 16/919,332

(22) Filed: Jul. 2, 2020

(65) Prior Publication Data
US 2022/0000418 A1      Jan. 6, 2022

(51) Int. Cl.
*A61B 5/00* (2006.01)
*B26B 21/40* (2006.01)
*G06T 7/00* (2017.01)

(52) U.S. Cl.
CPC ............ *A61B 5/445* (2013.01); *A61B 5/7278* (2013.01); *B26B 21/4031* (2013.01); *G06T 7/0012* (2013.01); *G06T 2207/30088* (2013.01)

(58) Field of Classification Search
CPC ......... A61B 5/7278; A61B 5/445; G06T 7/00; G06T 2207/20081; G06T 2207/30088;
(Continued)

(56) References Cited

U.S. PATENT DOCUMENTS 5,252,331 A    10/1993   Curtis et al.
9,013,567 B2    4/2015   Clemann et al.
(Continued)

FOREIGN PATENT DOCUMENTS

EP           3651949 A1     5/2020
WO      WO-2011106792 A2    9/2011
WO      WO-2019136354 A1    7/2019

OTHER PUBLICATIONS

Scienceinsider: Youtube video "What Are Ingrown Hairs—And How To Treat Them", Published Jun. 2, 2018. https://www.youtube.com/watch?v=laevAwpnPjc <https://www.youtube.com/watch?v=laevAwpnPjc> (Year: 2018).

*Primary Examiner* — Brenda C Bernardi
(74) *Attorney, Agent, or Firm* — Marshall, Gerstein & Borun LLP

(57) ABSTRACT

Digital imaging systems and methods are described for analyzing pixel data of an image of a shaving stroke for determining pressure being applied to a user's skin. A plurality of training images of a plurality of individuals are aggregated, each of the training images comprising pixel data of a respective individual when shaving with a shaving razor. A pressure model, trained with the pixel data, is operable to determine pressure being applied to the respective individual's skin. An image of a user when shaving with the shaving razor is received and analyzed, by the pressure model, to determine a user-specific pressure being applied to the user's skin by the shaving razor when a user shaving stroke is taken. A user-specific electronic recommendation to address at least one feature identifiable within the pixel data is generated and rendered, on a display screen of a user computing device.

25 Claims, 4 Drawing Sheets

(58) Field of Classification Search
CPC ......... G06T 7/0012; G06T 2207/20084; B26B 21/4031
See application file for complete search history.

(56) References Cited

U.S. PATENT DOCUMENTS

| | | |
|---|---|---|
| 2009/0024023 A1 | 1/2009 | Welches et al. |
| 2011/0016001 A1 | 1/2011 | Schieffelin |
| 2013/0231618 A1 | 9/2013 | Zupkosky et al. |
| 2017/0270593 A1* | 9/2017 | Sherman ............ G06Q 30/0251 |
| 2017/0330264 A1 | 11/2017 | Youssef et al. |
| 2018/0040053 A1 | 2/2018 | Robinson et al. |
| 2018/0247365 A1 | 8/2018 | Cook et al. |
| 2018/0349979 A1* | 12/2018 | Robinson .............. G06F 16/583 |
| 2018/0354147 A1* | 12/2018 | Goldfarb ............. B26B 21/4087 |
| 2019/0166980 A1 | 6/2019 | Huang et al. |
| 2019/0299437 A1* | 10/2019 | Fuellgrabe ............ B26B 19/388 |
| 2019/0355115 A1 | 11/2019 | Niebauer et al. |
| 2020/0202520 A1* | 6/2020 | Joyce ..................... A46B 13/02 |
| 2020/0294234 A1 | 9/2020 | Rance et al. |
| 2021/0368094 A1* | 11/2021 | Li ...................... H04N 5/23219 |

\* cited by examiner

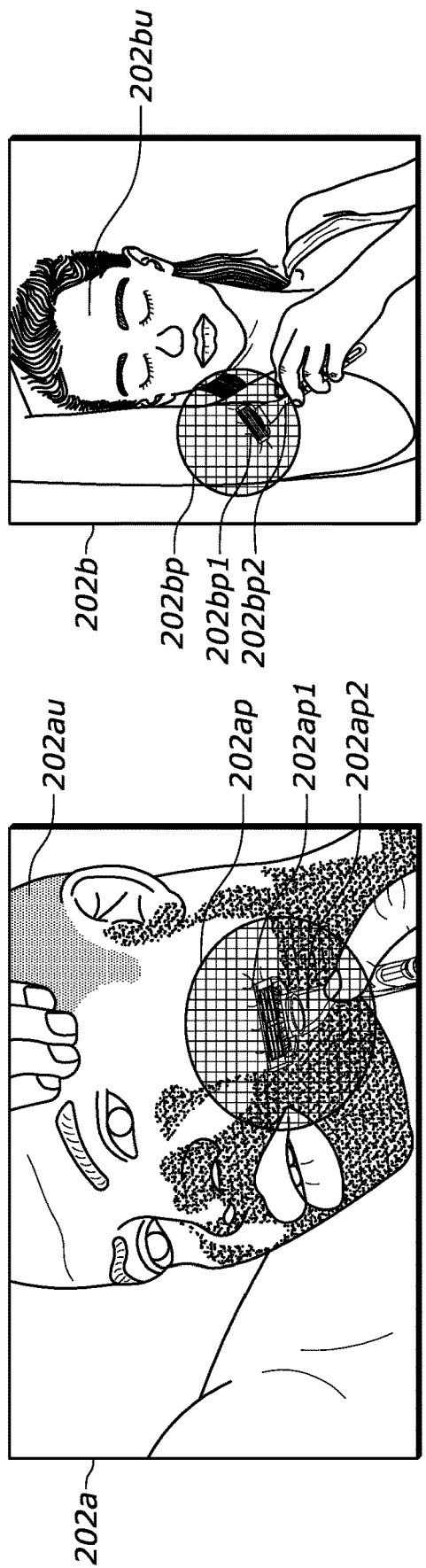
FIG. 2A
FIG. 2B
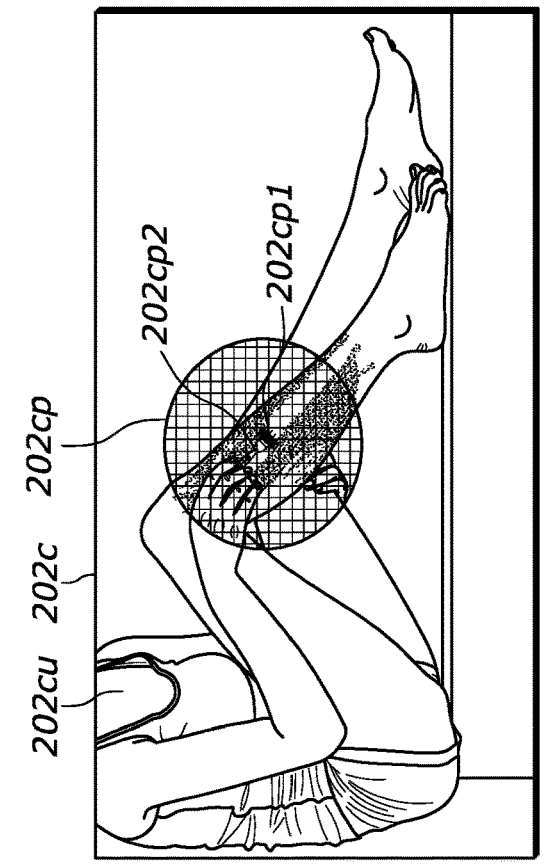
FIG. 2C

DIGITAL IMAGING SYSTEMS AND METHODS OF ANALYZING PIXEL DATA OF AN IMAGE OF A SHAVING STROKE FOR DETERMINING PRESSURE BEING APPLIED TO A USER'S SKIN

FIELD

The present disclosure generally relates to digital imaging systems and methods, and more particularly to, digital imaging systems and methods for analyzing pixel data of an image of a shaving stroke for determining pressure being applied to a user's skin.

BACKGROUND

Generally, shave performance can be summarized as a trade-off between closeness and irritation, where an individual typically can either achieve, on the one hand, an increased closeness of shave (removing more hair) but risking irritation or redness of his or her skin, or, on the other hand, a less close shave (leaving more hair) but reducing the risk of skin irritation. Individuals typically try to balance this trade-off to get their desired end result by manually regulating the quantity, direction and pressure (or load) of strokes applied during a shave. Taking an increased quantity of strokes, taking strokes going against the direction of hair growth or applying increased pressure during strokes will typically result in both increased closeness and increased risk of skin irritation. However, there is typically a threshold value for such shave parameters, going beyond this threshold value will yield minimal increase closeness benefit while yielding a high risk of unwanted skin irritation.

Thus a problem arises for existing shaving razors, and the use thereof, where individuals desiring a close shave generally apply too many strokes, too many strokes going against the hair growth direction and/or too much pressure (or load) during a shave session, under the false impression that it will improve the closeness of the end result. The problem is acutely pronounced given the various versions, brands, and types of shaving razors currently available to individuals, where each of the versions, brands, and types of shaving razors have different components, blades, sharpness, and/or otherwise different configurations, all of which can vary significantly in the quantity, direction and pressure (or load) of strokes required, and for each shaving razor type, to achieve a close shave (e.g., with little or no hair remaining) with little or no skin irritation. This problem is particularly acute because such existing shaving razors—which may be differently configured—provide little or no feedback or guidance to assist the individual achieve a close shave without skin irritation.

For the foregoing reasons, there is a need for digital imaging systems and methods for analyzing pixel data of an image of a shaving stroke for determining pressure being applied to a user's skin.

SUMMARY

Generally, as described herein, the digital systems and methods for analyzing pixel data of an image of a shaving stroke for determining pressure being applied to a user's skin, provide a digital imaging, and artificial intelligence (AI), based solution for overcoming problems that arise from incorrect use of different shaving razors. The digital systems and methods allow a user to submit a specific user image to imaging server(s) (e.g., including its one or more processors), or otherwise a computing device (e.g., such as locally on the user's mobile device), where the imaging server(s) or user computing device implements or executes a pressure model trained with pixel data of potentially 10,000s (or more) images of individuals using a shaving razor. The pressure model may generate, based on a determined user-specific pressure, a user-specific electronic recommendation designed to address at least one feature identifiable within the pixel data comprising at least a portion of the shaving razor applied to the user's skin. For example, the at least one feature can comprise pixels or pixel data indicative of an overage of pressure applied to the user's skin. In some embodiments, the user-specific recommendation (and/or product specific recommendation) may be transmitted via a computer network to a user computing device of the user for rendering on a display screen. In other embodiments, no transmission to the imaging server of the user's specific image occurs, where the user-specific recommendation (and/or product specific recommendation) may instead be generated by the pressure model, executing and/or implemented locally on the user's mobile device and rendered, by a processor of the mobile device, on a display screen of the mobile device. In various embodiments, such rendering may include graphical representations, overlays, annotations, and the like for addressing the feature in the pixel data.

More specifically, as describe herein, a digital imaging method of analyzing pixel data of an image of a shaving stroke for determining pressure being applied to a user's skin is disclosed. The digital imaging method comprises: (a) aggregating, at one or more processors communicatively coupled to one or more memories, a plurality of training images of a plurality of individuals, each of the training images comprising pixel data of a respective individual when shaving with a shaving razor. The digital imaging method may further comprise: (b) training, by the one or more processors with the pixel data of the plurality of training images, a pressure model operable to determine pressure being applied to the respective individual's skin by a shaving razor when a shaving stroke is taken. The digital imaging method may further comprise: (c) receiving, at the one or more processors, at least one image of a user when shaving with the shaving razor, where the at least one image is captured by a digital camera. The at least one image may comprise pixel data of at least a portion of the shaving razor applied to the user's skin. The digital imaging method may further comprise: (d) analyzing, by the pressure model executing on the one or more processors, the at least one image captured by the digital camera to determine a user-specific pressure being applied to the user's skin by the shaving razor when a user shaving stroke is taken. The digital imaging method may further comprise: (e) generating, by the one or more processors based on the user-specific pressure, at least one user-specific electronic recommendation designed to address at least one feature identifiable within the pixel data comprising the at least the portion of the shaving razor applied to the user's skin. The digital imaging method may further comprise: (f) rendering, on a display screen of a user computing device, the at least one user-specific recommendation.

In addition, as described herein, a digital imaging system is disclosed, configured to analyze pixel data of an image of a shaving stroke for determining pressure being applied to a user's skin. The digital imaging system may comprise an imaging server comprising a server processor and a server memory. The digital imaging system may further comprise an imaging application (app) configured to execute on a user computing device comprising a device processor and a device memory. The imaging app may be communicatively coupled to the imaging server. The digital imaging system may further comprise a pressure model trained with pixel data of a plurality of training images of individuals and operable to determine pressure being applied to a respective individual's skin by a shaving razor when a shaving stroke is taken. The pressure model may be configured to execute on the server processor or the device processor to cause the server processor or the device processor to receive at least one image of a user when shaving with the shaving razor. The at least one image may be captured by a digital camera. The at least one image comprises pixel data of at least a portion of the shaving razor applied to the user's skin. The pressure model may be further configured to execute on the server processor or the device processor to cause the server processor or the device processor to analyze, by the pressure model, the at least one image captured by the digital camera to determine a user-specific pressure being applied to the user's skin by the shaving razor when a user shaving stroke is taken. The pressure model may be further configured to execute on the server processor or the device processor to cause the server processor or the device processor to generate, based on the user-specific pressure, at least one user-specific electronic recommendation designed to address at least one feature identifiable within the pixel data comprising the at least the portion of the shaving razor applied to the user's skin. The pressure model may be further configured to execute on the server processor or the device processor to cause the server processor or the device processor to render, on a display screen of the user computing device of the user, the at least one user-specific recommendation.

Further, as described herein, a tangible, non-transitory computer-readable medium storing instructions for analyzing pixel data of an image of a shaving stroke for determining pressure being applied to a user's skin is disclosed. The instructions, when executed by one or more processors may cause the one or more processors to: (a) aggregate, at one or more processors communicatively coupled to one or more memories, a plurality of training images of a plurality of individuals, each of the training images comprising pixel data of a respective individual when shaving with a shaving razor; (b) train, by the one or more processors with the pixel data of the plurality of training images, a pressure model operable to determine pressure being applied to the respective individual's skin by a shaving razor when a shaving stroke is taken; (c) receive, at the one or more processors, at least one image of a user when shaving with the shaving razor, the at least one image captured by a digital camera, and the at least one image comprising pixel data of at least a portion of the shaving razor applied to the user's skin; (d) analyze, by the pressure model executing on the one or more processors, the at least one image captured by the digital camera to determine a user-specific pressure being applied to the user's skin by the shaving razor when a user shaving stroke is taken; (e) generate, by the one or more processors based on the user-specific pressure, at least one user-specific electronic recommendation designed to address at least one feature identifiable within the pixel data comprising the at least the portion of the shaving razor applied to the user's skin; and (f) render, on a display screen of a user computing device, the at least one user-specific recommendation.

In accordance with the above, and with the disclosure herein, the present disclosure includes improvements in computer functionality or in improvements to other technologies at least because the disclosure describes that, e.g., an imaging server, or otherwise computing device (e.g., a user computer device), is improved where the intelligence or predictive ability of the imaging server or computing device is enhanced by a trained (e.g., machine learning trained) pressure model. The pressure model, executing on the imaging server or computing device, is able to accurately identify, based on pixel data of other individuals, a user-specific pressure and a user-specific electronic recommendation designed to address at least one feature identifiable within the pixel data of a specific user comprising the at least the portion of the shaving razor applied to the user's skin. That is, the present disclosure describes improvements in the functioning of the computer itself or "any other technology or technical field" because an imaging server or user computing device is enhanced with a plurality of training images (e.g., 10,000s of training images and related pixel data as feature data) to accurately predict, detect, or determine pixel data of a user-specific images, such as newly provided customer images. This improves over the prior art at least because existing systems lack such predictive or classification functionality and are simply not capable of accurately analyzing user-specific images to output a predictive result to address at least one feature identifiable within the pixel data comprising the at least the portion of the shaving razor applied to the user's skin.

For similar reasons, the present disclosure relates to improvement to other technologies or technical fields at least because the present disclosure describes or introduces improvements to computing devices in the field of shaving razors, whereby the trained pressure model executing on the imaging device(s) or computing devices improve the field of shaving and/or shaving devices with digital and/or artificial intelligence based analysis of user or individual images to output a predictive result to address user-specific pixel data of at least one feature identifiable within the pixel data comprising the at least the portion of the shaving razor applied to the user's skin.

In addition, the present disclosure includes applying certain of the claim elements with, or by use of, a particular machine, e.g., a shaving razor, which appears in the images used to train the pressure model and further appears in the images submitted by a user to determine a user-specific pressure being applied to the user's skin by the shaving razor when a user shaving stroke is taken.

In addition, the present disclosure includes specific features other than what is well-understood, routine, conventional activity in the field, or adding unconventional steps that confine the claim to a particular useful application, e.g., analyzing pixel data of an image of a shaving stroke for determining pressure being applied to a user's skin as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 2A illustrates an example image and its related pixel data that may be used for training and/or implementing a pressure model, in accordance with various embodiments disclosed herein.

FIG. 2B illustrates a further example image and its related pixel data that may be used for training and/or implementing a pressure model, in accordance with various embodiments disclosed herein.

FIG. 2C illustrates a further example image and its related pixel data that may be used for training and/or implementing a pressure model, in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION OF THE INVENTION

Figure 1:
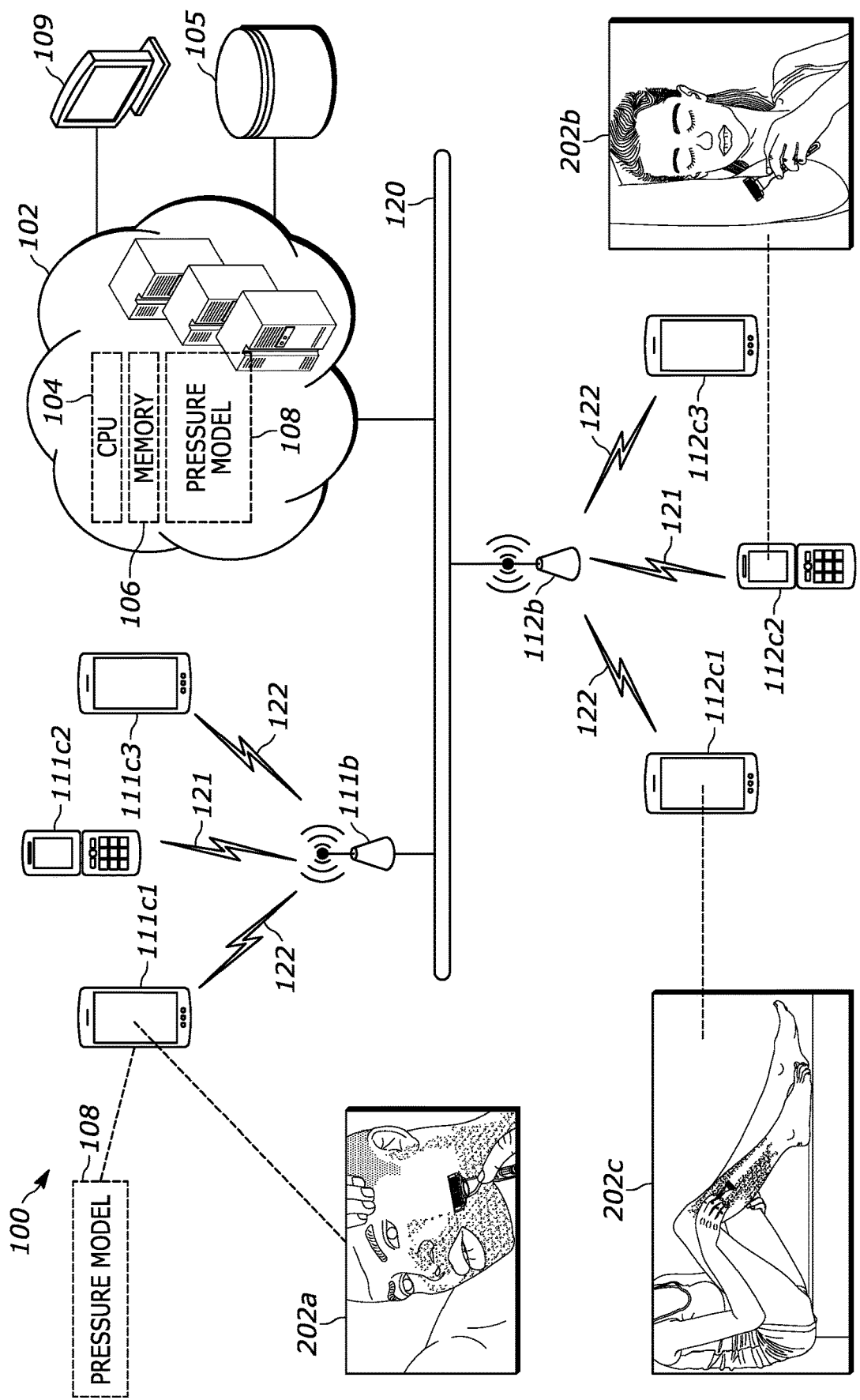
FIG. 1 illustrates an example digital imaging system configured to analyze pixel data of an image of a shaving stroke for determining pressure being applied to a user's skin, in accordance with various embodiments disclosed herein.

FIG. 1 illustrates an example digital imaging system 100 configured to analyze pixel data of an image (e.g., any one or more of images 202a, 202b, and/or 202c) of a shaving stroke for determining pressure being applied to a user's skin or body, in accordance with various embodiments disclosed herein. As referred to herein, a "body" may refer to any portion of the human body including the torso, waist, face, head, arm, leg, or other appendage or portion or part of the body thereof. In the example embodiment of FIG. 1, digital imaging system 100 includes server(s) 102, which may comprise one or more computer servers. In various embodiments server(s) 102 comprise multiple servers, which may comprise a multiple, redundant, or replicated servers as part of a server farm. In still further embodiments, server(s) 102 may be implemented as cloud-based servers, such as a cloud-based computing platform. For example, imaging server(s) 102 may be any one or more cloud-based platform(s) such as MICROSOFT AZURE, AMAZON AWS, or the like. Server(s) 102 may include one or more processor(s) 104 as well as one or more computer memories 106. Server(s) 102 may be referred to herein as "imaging server(s)."

The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memorie(s) 106 may store an operating system (OS) (e.g., Microsoft Windows, Linux, UNIX, etc.) capable of facilitating the functionalities, apps, methods, or other software as discussed herein. The memorie(s) 106 may also store a pressure model 108, which may be an artificial intelligence based model, such as a machine learning model, trained on various images (e.g., images 202a, 202b, and/or 202c), as described herein. Additionally, or alternatively, the pressure model 108 may also be stored in database 105, which is accessible or otherwise communicatively coupled to imaging server(s) 102. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the pressure model 108, where each may be configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 104 (e.g., a relational database, such as Oracle, DB2, MySQL, or a NoSQL based database, such as MongoDB). The data stored in the memories 106 and/or the database 105 may include all or part of any of the data or information described herein, including, for example, training images and/or user images (e.g., either of which including any one or more of images 202a, 202b, and/or 202c) or other information of the user, including demographic, age, race, skin type, or the like.

The imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some embodiments, imaging server(s) 102 may include a client-server platform technology such as ASP.NET, Java J2EE, Ruby on Rails, Node.js, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some embodiments, computer network 120 may comprise a private network or local area network (LAN). Additionally, or alternatively, computer network 120 may comprise a public network such as the Internet.

Imaging server(s) 102 may further include or implement an operator interface configured to present information to an administrator or operator and/or receive inputs from the administrator or operator. As shown in FIG. 1, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via or attached to imaging server(s) 102 or may be indirectly accessible via or attached to terminal 109. According to some embodiments, an administrator or operator may access the server 102 via terminal 109 to review information, make changes, input training data or images, and/or perform other functions.

As described above herein, in some embodiments, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, imaging server(s) 102 are communicatively connected, via computer network 120 to the one or more user computing devices 111c1-111c3 and/or 112c1-112c3 via base stations 111b and 112b. In some embodiments, base stations 111b and 112b may comprise cellular base stations, such as cell towers, communicating to the one or more user computing devices 111c1-111c3 and 112c1-112c3 via wireless communications 121 based on any one or more of various mobile phone standards, including NMT, GSM, CDMA, UMMTS, LTE, 5G, or the like. Additionally or alternatively, base stations 111b and 112b may comprise routers, wireless switches, or other such wireless connection points communicating to the one or more user computing devices 111c1-111c3 and 112c1-112c3 via wireless communications 122 based on any one or more of various wireless standards, including by non-limiting example, IEEE 802.11a/b/c/g (WIFI), the BLUETOOTH standard, or the like.

Any of the one or more user computing devices 111c1-111c3 and/or 112c1-112c3 may comprise mobile devices and/or client devices for accessing and/or communications with imaging server(s) 102. In various embodiments, user computing devices 111c1-111c3 and/or 112c1-112c3 may comprise a cellular phone, a mobile phone, a tablet device, a personal data assistance (PDA), or the like, including, by non-limiting example, an APPLE iPhone or iPad device or a GOOGLE ANDROID based mobile phone or table. In still further embodiments, user computing devices 111c1-111c3 and/or 112c1-112c3 may comprise a home assistant device and/or personal assistant device, e.g., having display screens, including, by way of non-limiting example, any one or more of a GOOGLE HOME device, an AMAZON ALEXA device, an ECHO SHOW device, or the like. In additional embodiments, user computing devices 111c1-111c3 and/or 112c1-112c3 may comprise a retail computing device. A retail computing device would be configured in the same or similar manner, e.g., as described herein for user computing devices 111c1-111c3, including having a processor and memory, for implementing, or communicating with (e.g., via server(s) 102), a pressure model 108 as described herein. However, a retail computing device may be located, installed, or otherwise positioned within a retail environment to allow users and/or customers of the retail environment to utilize the digital imaging systems and methods on site within the retail environment. For example, the retail computing device may be installed within a kiosk for access by a user. The user may then upload or transfer images (e.g., from a user mobile device) to the kiosk to implement the digital imaging systems and methods described herein. Additionally, or alternatively, the kiosk may be configured with a camera to allow the user to take new images (e.g., in a private manner where warranted) of himself or herself for upload and transfer. In such embodiments, the user or consumer himself or herself would be able to use the retail computing device to receive and/or have rendered a user-specific electronic recommendation, as described herein, on a display screen of the retail computing device. Additionally, or alternatively, the retail computing device may be a mobile device (as described herein) as carried by an employee or other personnel of the retail environment for interacting with users or consumers on site. In such embodiments, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a user-specific electronic recommendation, as described herein, on a display screen of the retail computing device. In addition, the one or more user computing devices 111c1-111c3 and/or 112c1-112c3 may implement or execute an operating system (OS) or mobile platform such as Apple's iOS and/or Google's Android operation system. Any of the one or more user computing devices 111c1-111c3 and/or 112c1-112c3 may comprise one or more processors and/or one or more memories for storing, implementing, or executing computing instructions or code, e.g., a mobile application or a home or personal assistant application, as described in various embodiments herein. As shown in FIG. 1, pressure model 108 may also be stored locally on a memory of a user computing device (e.g., user computing device 111c1).

User computing devices 111c1-111c3 and/or 112c1-112c3 may comprise a wireless transceiver to receive and transmit wireless communications 121 and/or 122 to and from base stations 111b and/or 112b. Pixel based images 202a, 202b, and/or 202c may be transmitted via computer network 120 to imaging server(s) 102 for training of model(s) and/or imaging analysis as describe herein.

In addition, the one or more user computing devices 111c1-111c3 and/or 112c1-112c3 may include a digital camera and/or digital video camera for capturing or taking digital images and/or frames (e.g., which can be any one or more of images 202a, 202b, and/or 202c). Each digital image may comprise pixel data for training or implementing model(s), such as AI or machine learning models, as described herein. For example, a digital camera and/or digital video camera of, e.g., any of user computing devices 111c1-111c3 and/or 112c1-112c3, may be configured to take, capture, or otherwise generate digital images (e.g., pixel based images 202a, 202b, and/or 202c) and, at least in some embodiments, may store such images in a memory of a respective user computing devices.

Still further, each of the one or more user computer devices 111c1-111c3 and/or 112c1-112c3 may include a display screen for displaying graphics, images, text, product recommendations, data, pixels, features, and/or other such visualizations or information as described herein. In various embodiments, graphics, images, text, product recommendations, data, pixels, features, and/or other such visualizations or information may be received by imaging server(s) 102 for display on the display screen of any one or more of user computer devices 111c1-111c3 and/or 112c1-112c3. Additionally, or alternatively, a user computer device may comprise, implement, have access to, render, or otherwise expose, at least in part, an interface or a guided user interface (GUI) for displaying text and/or images on its display screen.

FIGS. 2A-2C illustrate example images 202a, 202b, and 202c that may be collected or aggregated at imaging server(s) 102 and may be analyzed by, and/or used to train, a pressure model (e.g., an AI model such as a machine learning imaging model as describe herein). Each of these images may comprise pixel data (e.g., RGB data) corresponding representing feature data and corresponding to each of the personal attributes of the respective users 202au, 202bu, and 202cu, within the respective image. The pixel data may be captured by a digital camera of one of the user computing devices (e.g., one or more user computer devices 111c1-111c3 and/or 112c1-112c3).

Generally, as described herein, pixel data (e.g., pixel data 202ap, 202bp, and/or 202cp) comprises individual points or squares of data within an image, where each point or square represents a single pixel (e.g., pixel 202ap1 and pixel 202ap2) within an image. Each pixel may be a specific location within an image. In addition, each pixel may have a specific color (or lack thereof). Pixel color, may be determined by a color format and related channel data associated with a given pixel. For example, a popular color format includes the red-green-blue (RGB) format having red, green, and blue channels. That is, in the RGB format, data of a pixel is represented by three numerical RGB components (Red, Green, Blue), that may be referred to as a channel data, to manipulate the color of pixel's area within the image. In some implementations, the three RGB components may be represented as three 8-bit numbers for each pixel. Three 8-bit bytes (one byte for each of RGB) is used to generate 24 bit color. Each 8-bit RGB component can have 256 possible values, ranging from 0 to 255 (i.e., in the base 2 binary system, an 8 bit byte can contain one of 256 numeric values ranging from 0 to 255). This channel data (R, G, and B) can be assigned a value from 0 255 and be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values. So (Red=220, Green=220, Blue=220) is a light gray (near white), and (Red=40, Green=40, Blue=40) is a dark gray (near black).

In this way, the composite of three RGB values creates the final color for a given pixel. With a 24-bit RGB color image using 3 bytes there can be 256 shades of red, and 256 shades of green, and 256 shades of blue. This provides 256×256×256, i.e., 16.7 million possible combinations or colors for 24 bit RGB color images. In this way, the pixel's RGB data value shows how much of each of Red, and Green, and Blue pixel is comprised of. The three colors and intensity levels are combined at that image pixel, i.e., at that pixel location on a display screen, to illuminate a display screen at that location with that color. In is to be understood, however, that other bit sizes, having fewer or more bits, e.g., 10-bits, may be used to result in fewer or more overall colors and ranges.

As a whole, the various pixels, positioned together in a grid pattern, form a digital image (e.g., pixel data 202ap, 202bp, and/or 202cp). A single digital image can comprise thousands or millions of pixels. Images can be captured, generated, stored, and/or transmitted in a number of formats, such as JPEG, TIFF, PNG and GIF. These formats use pixels to store represent the image.

FIG. 2A illustrates an example image 202a and its related pixel data (e.g., pixel data 202ap) that may be used for training and/or implementing a pressure model (e.g., pressure model 108), in accordance with various embodiments disclosed herein. Example image 202a illustrates a user 202au or individual taking a shaving stroke, with a shaving razor, at a body area location comprising the user's cheek. Image 202a is comprised of pixel data, including pixel data 202ap. Pixel data 202ap includes a plurality of pixels including pixel 202ap1 and pixel 202ap2. Pixel 202ap1 is a dark pixel (e.g., a pixel with low R, G, and B values) positioned in image 202a where user 202au applies pressure to his cheek area with a shaving razor. Pixel 202ap2 is a pixel positioned in image 202a comprising a handle portion of the shaving razor. Pixel data 202ap includes various remaining pixels including remaining portions of the shaving razor and other areas of the user's cheek where pressure is applied. Pixel data 202ap further includes pixels representing further features including the shaving stroke, shaving cream affected by the shaving stroke, depression of the user's skin, the user's hand, and other features as shown in FIG. 2A.

FIG. 2B illustrates a further example image 202b and its related pixel data (e.g., pixel data 202bp) that may be used for training and/or implementing a pressure model (e.g., pressure model 108), in accordance with various embodiments disclosed herein. Example image 202b illustrates a user 202bu or individual taking a shaving stroke, with a shaving razor, at a body area location comprising the user's underarm. Image 202*b* is comprised of pixel data, including pixel data 202*bp*. Pixel data 202*bp* includes a plurality of pixels including pixel 202*bp*1 and pixel 202*bp*2. Pixel 202*bp*1 is a dark pixel (e.g., a pixel with low R, G, and B values) positioned in image 202*b* where user 202*au* applies pressure to her underarm area with a shaving razor. Pixel 202*bp*2 is a pixel positioned in image 202*b* comprising a neck portion of the shaving razor. Pixel data 202*ap* includes various remaining pixels including remaining portions of the shaving razor and other areas of the user's underarm where pressure is applied. Pixel data 202*bp* further includes pixels representing further features including the shaving stroke, shaving cream affected by the shaving stroke, depression of the user's skin, the user's arm, hand position, and other features as shown in FIG. 2B.

FIG. 2C illustrates a further example image 202*cu* and its related pixel data (e.g., 202*cp*) that may be used for training and/or implementing a pressure model (e.g., pressure model 108), in accordance with various embodiments disclosed herein. Example image 202*c* illustrates a user 202*cu* or individual taking a shaving stroke, with a shaving razor, at a body area location comprising the user's leg. Image 202*c* is comprised of pixel data, including pixel data 202*cp*. Pixel data 202*cp* includes a plurality of pixels including pixel 202*cp*1 and pixel 202*cp*2. Pixel 202*cp*1 is a dark pixel (e.g., a pixel with low R, G, and B values) positioned in image 202*c* where user 202*cu* applies pressure to her leg area with a shaving razor. Pixel 202*cp*2 is a pixel positioned in image 202*c* comprising a handle portion of the shaving razor. Pixel data 202*cp* includes various remaining pixels including remaining portions of the shaving razor and other areas of the user's leg where pressure is applied. Pixel data 202*cp* further includes pixels representing further features including the shaving stroke, shaving cream affected by the shaving stroke, depression of the user's skin, the user's leg, hand position, and other features as shown in FIG. 2C.

Figure 3:
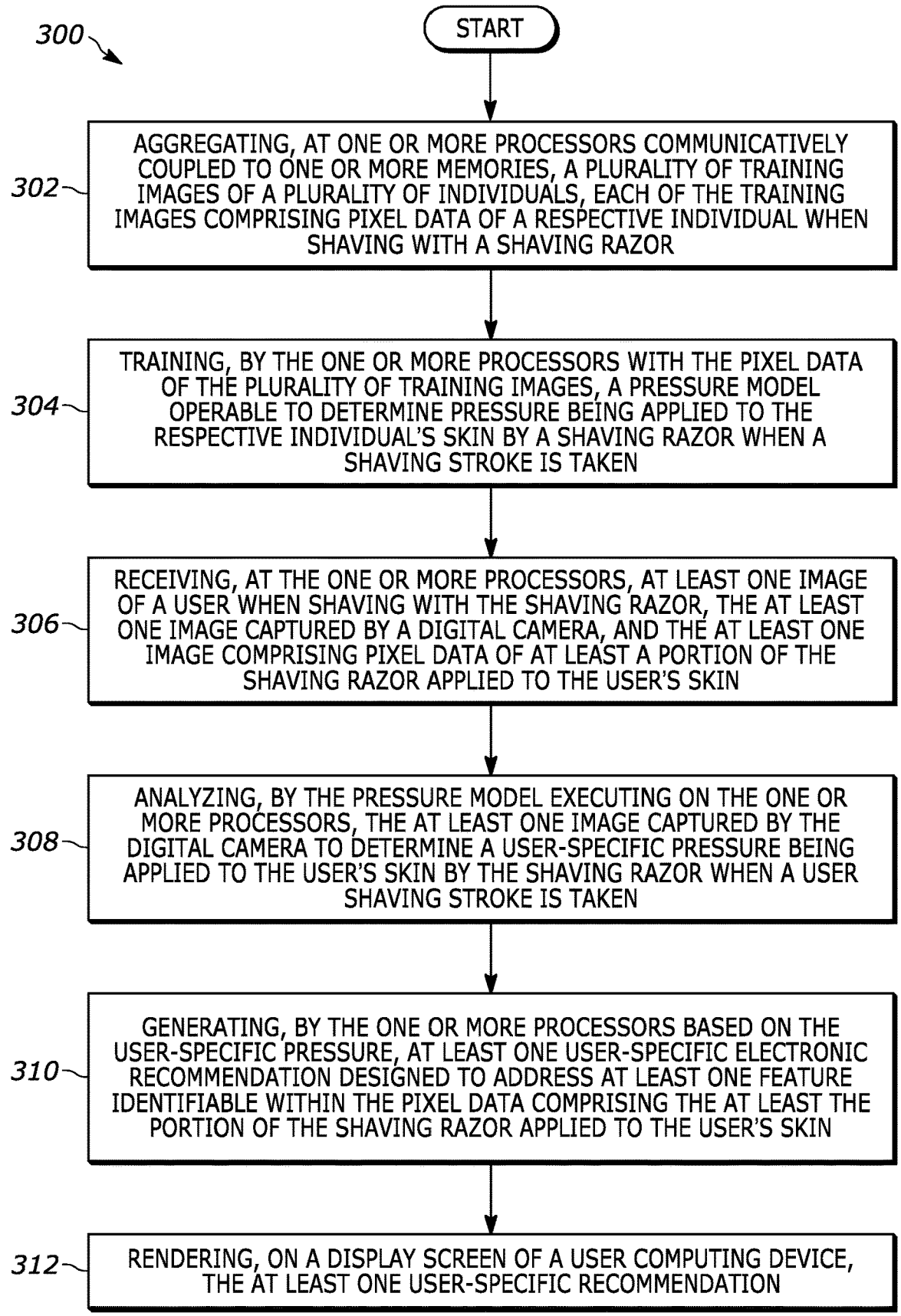
FIG. 3 illustrates a diagram of a digital imaging method of analyzing pixel data of an image of a shaving stroke for determining pressure being applied to a user's skin, in accordance with various embodiments disclosed herein.

FIG. 3 illustrates a diagram of a digital imaging method 300 of analyzing pixel data of an image (e.g., any of images 202*a*, 202*b*, and/or 202*c*) of a shaving stroke for determining pressure being applied to a user's skin, in accordance with various embodiments disclosed herein. Images, as described herein, are generally pixel images as captured by a digital camera (e.g., a digital camera of user computing device 111*c*1). In some embodiments an image may comprise or refer to a plurality of images such as a plurality of images (e.g., frames) as collected using a digital video camera. Frames comprise consecutive images defining motion, and can comprise a movie, a video, or the like.

At block 302, method 300 comprises aggregating, at one or more processors communicatively coupled to one or more memories, a plurality of training images of a plurality of individuals, each of the training images comprising pixel data of a respective individual when shaving with a shaving razor. In some embodiments, the shaving razor may be a wet razor. In other embodiments, the shaving razor may be a dry shaver. Additionally, or alternatively, the shaving razor may be an electric razor, which may be a wet or dry shaving razor.

At block 304, method 300 comprises training, by the one or more processors with the pixel data of the plurality of training images, a pressure model (e.g., pressure model 108) operable to determine pressure being applied to the respective individual's skin by a shaving razor when a shaving stroke is taken. In various embodiments, pressure model is an artificial intelligence (AI) based model trained with at least one AI algorithm. Training of pressure model 108 involves image analysis of the training images to configure weights of pressure model 108, and its underlying algorithm (e.g., machine learning or artificial intelligence algorithm) used to predict and/or classify future images. For example, in various embodiments herein, generation of pressure model 108 involves training pressure model 108 with the plurality of training images of a plurality of individuals, where each of the training images comprise pixel data of a respective individual when shaving with a shaving razor. In some embodiments, one or more processors of a server or a cloud-based computing platform (e.g., imaging server(s) 102) may receive the plurality of training images of the plurality of individuals via a computer network (e.g., computer network 120). In such embodiments, the server and/or the cloud-based computing platform may train the pressure model with the pixel data of the plurality of training images.

In various embodiments, a machine learning imaging model, as described herein (e.g. pressure model 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms may be included as a library or package executed on imaging server(s) 102. For example, libraries may include the TENSORFLOW based library, the PYTORCH library, and/or the SCIKIT-LEARN Python library.

Machine learning may involve identifying and recognizing patterns in existing data (such as training a model based on pixel data within images having pixel data of a respective individual when shaving with a shaving razor) in order to facilitate making predictions or identification for subsequent data (such as using the model on new pixel data of a new individual in order to determine a user-specific pressure being applied to the specific user's skin by the shaving razor when a user shaving stroke is taken).

Machine learning model(s), such as the pressure model described herein for some embodiments, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Image analysis may include training a machine learning based model (e.g., the pressure model) on pixel data of images of one or more individuals taking shaving strokes with shaving razors. Additionally, or alternatively, image analysis may include using a machine learning imaging model, as previously trained, to determine, based on the pixel data (e.g., including their RGB values) one or more images of the individual(s), a user-specific pressure being applied to the user's skin by the shaving razor when a user shaving stroke is taken. The weights of the model may be trained via analysis of various RGB values of individual pixels of a given image. For example, dark or low RGB values (e.g., a pixel with values R=25, G=28, B=31) may indicate a pressed or loaded area of the user's skin. A red toned RGB value (e.g., a pixel with values R=215, G=90, B=85) may indicate irritated skin. A lighter RGB values (e.g., a pixel with R=181, G=170, and B=191) may indicate a lighter value, such as a normal skin tone color. Together, when a pixel with a red toned RGB value and/or a pixel with a dark or low RGB value is positioned within a given image, or is otherwise surrounded by, a group or set of pixels having skin toned colors, then that may indicate an area on the skin where irritation or pressure occurs, respectively, as identified within the given image. In this way, pixel data (e.g., detailing one or more features of an individual, such as areas of pressure applied by a shaving razor or identification of the shaving razor or its portions) of 10,000s training images may be used to train or use a machine learning imaging model to determine a user-specific pressure being applied to the user's skin by the shaving razor when a user shaving stroke is taken.

In some embodiments training, by the one or more processors (e.g., of imaging server(s) 102) with the pixel data of the plurality of training images, the pressure model (e.g., pressure model 108) comprises training the pressure model (e.g., pressure model 108) to detect an amount of depression of the user's skin to determine the user-specific pressure being applied to the user's skin by the shaving razor when the shaving stroke is taken. In such embodiments the pressure model may be trained to recognize that pixels with darker values (e.g., darker or lower RGB values) indicate a pressure area. For example, for image 202*a*, pixel 202*ap*1 is a dark pixel positioned in image 202*a* where user 202*au* applies pressure to his cheek area with a shaving razor. Pixel 202*ap*2 is a pixel positioned in image 202*a* comprising a handle portion of the shaving razor. Pixel data 202*ap* includes various remaining pixels including remaining portions of the shaving razor and other areas of the user's cheek where pressure is applied. Pressure model 108 may be trained to recognize (by assigning greater weighs to darker pixels) that such darker pixels (e.g., pixel 202*ap*1) against a pixel or group pixels having skin tone colors indicates that pressure is being applied to skin. Similarly, pressure model 108 may be trained to recognize (by assigning greater weighs to nearby angular pixels) that such nearby angular pixels (e.g., pixel 202*ap*2) represents a shaving razor handle.

In this way the pressure model can identify patterns within the pixel data to determine user-specific pressure being applied to a user's skin by a shaving razor when a user shaving stroke is taken.

Additionally, or alternatively, training, by the one or more processors (e.g., of imaging server(s) 102) with the pixel data of the plurality of training images, the pressure model (e.g., pressure model 108) may comprise training the pressure model (e.g., pressure model 108) to detect an angle of a razor cartridge with respect to a razor handle of the shaving razor to determine user-specific pressure being applied to the user's skin by the shaving razor when the shaving stroke is taken. In such embodiments, multiple pixels distributed across a razor handle of an image (e.g., including pixel 202*ap*2 for image 202*a*) may be detected, e.g., in an angled pattern having a similar RGB color scheme. In this way the pressure model 108 can detect, based on pixels related to the razor handle, an angle of a razor cartridge with respect to a razor handle of the shaving razor. The identification of the angle and positioning of the razor handle (and thereby the razor cartridge) are features or parameters that allow the pressure model (e.g., pressure model 108) to determine user-specific pressure being applied to the user's skin by the shaving razor when the shaving stroke is taken.

In some embodiments, both pressure of the user's skin and angle of the razor handle/razor cartridge may be used to train pressure model 108. For example, in such embodiments, training, by the one or more processors (e.g., imaging server(s) 102) with the pixel data of the plurality of training images, the pressure model (e.g., pressure model 108) may comprise training the pressure model (e.g., pressure model 108) to detect an amount of depression of the user's skin (as described above herein) in combination with an angle of a razor cartridge with respect to a razor handle of the shaving razor (as described above herein) to determine the user-specific pressure being applied the a user's skin by the shaving razor when the shaving stroke is taken.

In various embodiments, a pressure model (e.g., pressure model 108) may be further trained, by one or more processors (e.g., imaging server(s) 102), with the pixel data of the plurality of training images, to output one or more location identifiers indicating one or more corresponding body area locations of respective individuals. In such embodiments, the pressure model (e.g., pressure model 108), executing on the one or more processors (e.g., imaging server(s) 102) and analyzing the at least one image of the user, can determine a location identifier indicating a body area location of the user's body or body area. For example, body area locations may comprise a user's cheek, a user's neck, a user's head, a user's groin, a user's underarm, a user's chest, a user's back, a user's leg, a user's arm, or a user's bikini area. For example, each of images image 202*a*, 202*b*, and 202*c* illustrate example body area locations including a user's check, a user's underarm or armpit, and a user's leg, respectively.

Additionally, or alternatively, training, by the one or more processors (e.g., of imaging server(s) 102) with the pixel data of the plurality of training images, the pressure model (e.g., pressure model 108) may comprise training the pressure model (e.g., pressure model 108) to detect an amount of depression of the user's skin in combination with a direction in which a razor handle of the shaving razor is oriented relative to a body area of the user to determine the user-specific pressure being applied the a user's skin by the shaving razor when the shaving stroke is taken. In such embodiments, multiple pixels distributed across a razor handle of an image (e.g., including pixel 202*ap*2 for image 202a) may be detected, e.g., in an angled pattern having a similar RGB color scheme. The detected pixels may be compared with a body area (e.g., a chin or neck) to determine the orientation of the shaving razor to the body area. For example, the pixel data could indicate that a razor handle is orientated with a non-cartridge/razor end in an upwards orientation (upstroke) with respect to the chin or neck area. Alternatively, the pixel data could indicate that a razor handle is orientated with a non-cartridge/razor end in a downwards orientation (down stroke) with respect to the chin or neck area. Other such orientations could include a sideways orientation and/or related degrees thereof. In this way the pressure model 108 can detect, based on pixels related to the razor handle oriented relative to a body area of the user, a direction in which a razor handle is moving or is otherwise oriented. The identification of the orientation and direction of the razor handle (and thereby the razor cartridge) relative to the body area are features or parameters that allow the pressure model (e.g., pressure model 108) to determine user-specific pressure being applied to the user's skin by the shaving razor when the shaving stroke is taken.

Additionally, or alternatively, training, by the one or more processors (e.g., of imaging server(s) 102) with the pixel data of the plurality of training images, the pressure model (e.g., pressure model 108) may comprise training the pressure model (e.g., pressure model 108) to detect an amount of depression of the user's skin in combination with a hand grip pattern of the user on a razor handle of the shaving razor to determine the user-specific pressure being applied the a user's skin by the shaving razor when the shaving stroke is taken. In such embodiments, multiple pixels distributed across a razor handle of an image (e.g., including pixel 202ap2 for image 202a) may be detected, e.g., in an angled pattern having a similar RGB color scheme. The detected pixels may be compared with an identified hand grip pattern (e.g., identification of fingers on the razor handle) to determine pressure being applied to the user skin. For example, a strong grip pattern (e.g., more fingers detected on the razor handle within the pixel data) could indicate more pressure is applied to the user's skin and vice versa. In this way the pressure model 108 can detect, based on pixels comprising a hand grip pattern of the user on the razor handle of the shaving razor, pressure applied. The hand grip pattern and razor handle are features or parameters that allow the pressure model (e.g., pressure model 108) to determine user-specific pressure being applied to the user's skin by the shaving razor when the shaving stroke is taken.

With reference to FIG. 3, at block 306 method 300 comprises receiving, at the one or more processors (e.g., imaging server(s) 102 and/or a user computing device, such as user computing device 111c1), at least one image of a user when shaving with the shaving razor. The at least one image may have been captured by a digital camera. In addition, the at least one image may comprise pixel data of at least a portion of the shaving razor applied to the user's skin.

At block 308, method 300 comprises analyzing, by the pressure model (e.g., pressure model 108) executing on the one or more processors (e.g., imaging server(s) 102 and/or a user computing device, such as user computing device 111c1), the at least one image captured by the digital camera to determine a user-specific pressure being applied to the user's skin by the shaving razor when a user shaving stroke is taken.

At block 310, method 300 comprises generating, by the one or more processors (e.g., imaging server(s) 102 and/or a user computing device, such as user computing device 111c1) based on the user-specific pressure, at least one user-specific electronic recommendation designed to address at least one feature identifiable within the pixel data comprising the at least the portion of the shaving razor applied to the user's skin.

At block 312, method 300 comprises rendering, on a display screen of a user computing device, the at least one user-specific recommendation. A user computing device may comprise at least one of a mobile device, a tablet, a handheld device, or a desktop device, for example, as described herein for FIG. 1. In some embodiments, the user computing device (e.g., user computing device 111c1) may receive the at least one image comprising the pixel data of the at least a portion of the shaving razor applied to the user's skin. In such embodiments, the user computing device may execute the pressure model (e.g., pressure model 108) locally and generate, based on output of the pressure model (e.g., pressure model 108), the user-specific recommendation. The user computing device 111c1 may then render the user-specific recommendation on its display screen.

Additionally, or alternatively, in other embodiments, the imaging server(s) 102 may analyze the user image remote from the user computing device to determine the user-specific pressure and/or user-specific electronic recommendation designed to address at least one feature identifiable within the pixel data comprising the at least the portion of the shaving razor applied to the user's skin. For example, in such embodiments imaging server or a cloud-based computing platform (e.g., imaging server(s) 102) receives, across computer network 120, the at least one image comprising the pixel data of at the least a portion of the shaving razor applied to the user's skin. The server or a cloud-based computing platform may then execute pressure model (e.g., pressure model 108) and generate, based on output of the pressure model (e.g., pressure model 108), the user-specific recommendation. The server or a cloud-based computing platform may then transmit, via the computer network (e.g., computer network 120), the user-specific recommendation to the user computing device for rendering on the display screen of the user computing device In some embodiments, the user may submit a new image to the pressure model for analysis as described herein. In such embodiments, one or more processors (e.g., imaging server(s) 102 and/or a user computing device, such as user computing device 111c1) may receive a new image of the user when shaving with the shaving razor. The new image may been captured by a digital camera of user computing device 111c1. The new image may comprise pixel data of at least a portion of the shaving razor applied to the user's skin. The pressure model (e.g., pressure model 108) may then analyze, on the one or more processors (e.g., imaging server(s) 102 and/or a user computing device, such as user computing device 111c1), the new image captured by the digital camera to determine a new user-specific pressure being applied to the user's skin by the shaving razor when a new user shaving stroke is taken. A new user-specific electronic recommendation or comment may be generated, based on the new user-specific pressure, regarding at least one feature identifiable within the pixel data of the new image. The new user-specific recommendation or comment (e.g., message) may then be rendered on a display screen of a user computing device of the user.

In some embodiments, a user-specific electronic recommendation may be displayed on the display screen of a user computing device (e.g., user computing device 111c1) with a graphical representation of the user's skin as annotated with one or more graphics or textual renderings corresponding to the user-specific pressure. In still further embodiments, the at least one user-specific electronic recommendation may be rendered in real-time or near-real time during or after the user shaving stroke is taken.

In additional embodiments, a user-specific electronic recommendation may comprise a product recommendation for a manufactured product. In such embodiments, the user-specific electronic recommendation may be displayed on the display screen of a user computing device (e.g., user computing device 111c1) with instructions (e.g., a message) for treating, with the manufactured product, the at least one feature identifiable in the pixel data comprising the at least the portion of the shaving razor applied to the user's skin. In still further embodiments, either the user computing device 111c1 and/or imaging server(s) may initiate, based on the product recommendation, the manufactured product for shipment to the user.

With regard to manufactured product recommendations, in some embodiments, one or more processors (e.g., imaging server(s) 102 and/or a user computing device, such as user computing device 111c1) may generate a modified image based on the at least one image of the user, e.g., as originally received. In such embodiments, the modified image may depict a rendering of how the user's skin is predicted to appear after treating the at least one feature with the manufactured product. For example, the modified image may be modified by updating, smoothing, or changing colors of the pixels of the image to represent a possible or predicted change after treatment of the at least one feature within the pixel data with the manufactured product. The modified image may then be rendered on the display screen of the user computing device (e.g., user computing device 111c1).

Additionally, or alternatively, a recommendation may be also made for the shaving razor shown in the at least one image of the user, e.g., as originally received. In such embodiments, a user-specific electronic recommendation may displayed on the display screen of the user computing device (e.g., user computing device 111c1) with instructions for treating, with the shaving razor (e.g., as shown in the original image), the at least one feature identifiable in the pixel data comprising the at least the portion of the shaving razor applied to the user's skin.

Figure 4:
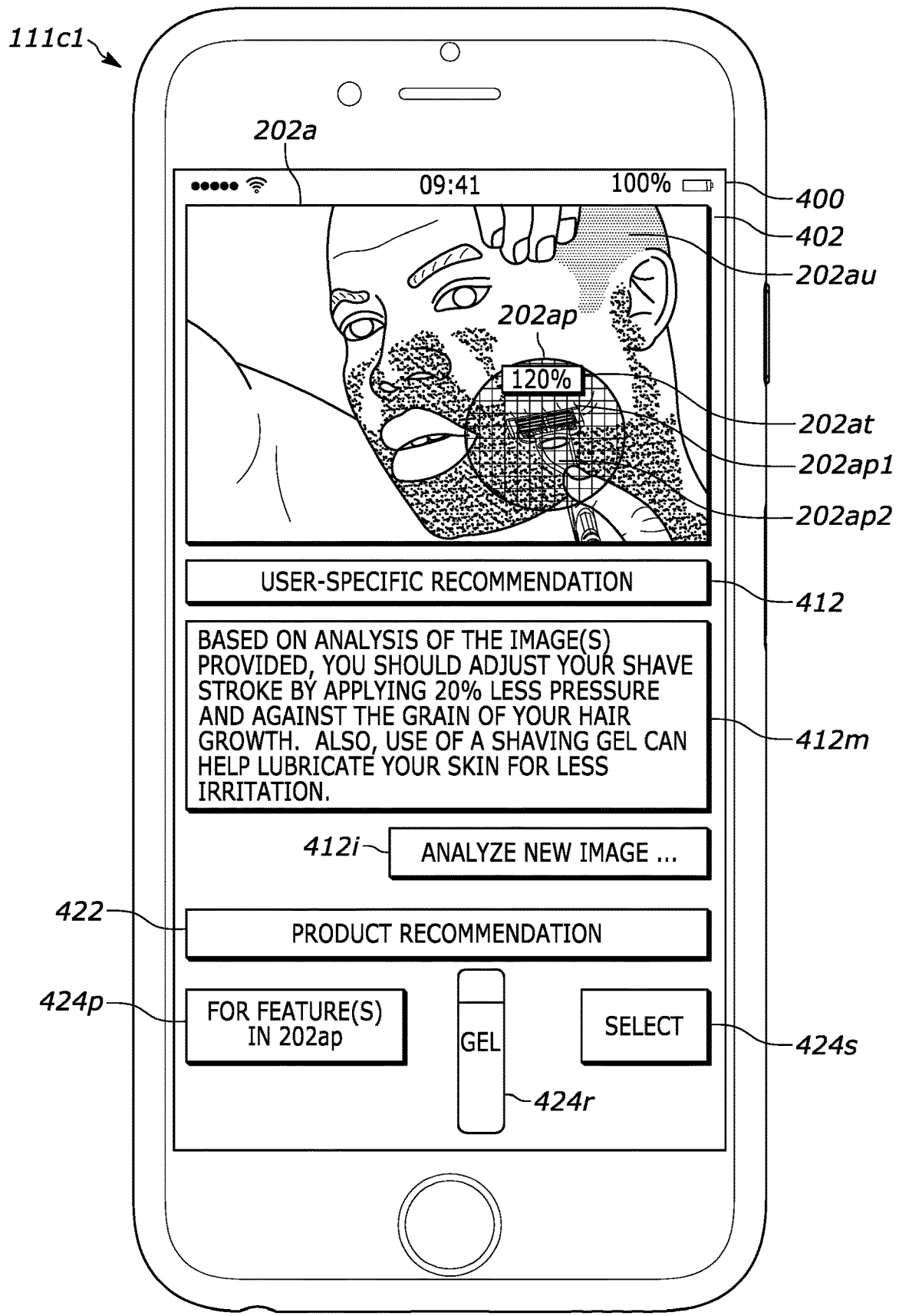
FIG. 4 illustrates an example user interface as rendered on a display screen of a user computing device in accordance with various embodiments disclosed herein.

FIG. 4 illustrates an example user interface 402 as rendered on a display screen 400 of a user computing device 111c1 in accordance with various embodiments disclosed herein. For example, as shown in the example of FIG. 4, user interface 402 may be implemented or rendered via an application (app) executing on user computing device 111c1.

For example, as shown in the example of FIG. 4, user interface 402 may be implemented or rendered via a native app executing on user computing device 111c1. In the example of FIG. 4, user computing device 111c1 is a user computer device as described for FIG. 1, e.g., where 111c1 is illustrated as an APPLE iPhone that implements the APPLE iOS operating system and has display screen 400. User computing device 111c1 may execute one or more native applications (apps) on its operating system. Such native apps may be implemented or coded (e.g., as computing instructions) in a computing language (e.g., SWIFT) executable by the user computing device operating system (e.g., APPLE iOS) by the processor of user computing device 111c1.

Additionally, or alternatively, user interface 402 may be implemented or rendered via a web interface, such as via a web browser application, e.g., Safari and/or Google Chrome app(s), or other such web browser or the like.

As shown in the example of FIG. 4, user interface 402 comprises a graphical representation (e.g., image 202a) of the user's skin. Image 202a may be the at least one image of the user (or graphical representation thereof) when shaving with the shaving razor and as analyzed by the pressure model (e.g., pressure model 108) as described herein. In the example of FIG. 4, graphical representation (e.g., image 202a) of the user's skin is annotated with one or more graphics (e.g., area of pixel data 202ap) or textual rendering (e.g., text 202at) corresponding to the user-specific pressure. For example, the area of pixel data 202ap may be annotated or overlaid on top of the image of the user (e.g., image 202a) to highlight the area or feature(s) identified within the pixel data (e.g., feature data and/or raw pixel data) by the pressure model (e.g., pressure model 108). In the example of FIG. 4, the area of pixel data 202ap and the feature(s) identified within include the user-specific pressure the user is applying with his shaving stroke, the shaving razor, the depression of the user's skin, irritation of the skin, skin type, skin tone, direction of the shaving stroke with respect to hair grain, and other features shown in area of pixel data 202ap. In various embodiments, the pixels identified as the specific features indicating pressure (e.g., pixel 202ap1 as a dark pixel indicating where pressure is applied) or causing pressure (e.g., e.g., pixel 202ap2 indicating the handle or neck of the razor causing pressure) may be highlighted or otherwise annotated when rendered.

Textual rendering (e.g., text 202at) shows a user-specific pressure value (e.g., 120%) which illustrates that the user is applying 120% of a needed or recommended pressure for the given shaving stroke. The 120% value indicates that the user is applying too much pressure that will likely lead to skin irritation. It is to be understood that other textual rendering types or values are contemplated herein, where textual rendering types or values may be rendered, for example, as pressure values in, e.g., Pascal (Pa) values, newton per square meter (N/m2) values, pounds per square inch (psi), or the like. Additionally, or alternatively, color values may use and/or overlaid on a graphical representation shown on user interface 402 (e.g., image 202a) to indicate too much pressure, too little pressure, or pressure within acceptable ranges (e.g., 95% to 103% pressure).

User interface 402 may also include or render a user-specific electronic recommendation 412. In the embodiment of FIG. 4, user-specific electronic recommendation 412 comprises a message 412m to the user designed to address at least one feature identifiable within the pixel data comprising the portion of the shaving razor applied to the user's skin. As shown in the example of FIG. 4, message 412m recommends to the user to apply less pressure (e.g., 20% less pressure) and to apply the shaving stroke against the skin of the user.

Message 412m further recommends use of a shaving gel to reduce skin irritation. The shaving gel recommendation can be made based on the high pressure value (e.g., 120%) that the user is applying where the shaving gel product is designed to address the issue of skin irritation detected in the pixel data of image 202a or otherwise assumed based on the high pressure value. The product recommendation can be correlated to the identified feature within the pixel data, and the user computing device 111c1 and/or server(s) 102 can be instructed to output the product recommendation when the feature (e.g., excessive pressure or skin irritation) is identified.

User interface 402 also include or render a section for a product recommendation 422 for a manufactured product 424r (e.g., shaving gel as described above). The product recommendation 422 generally corresponds to the user-specific electronic recommendation 412, as described above.

For example, in the example of FIG. 4, the user-specific electronic recommendation 412 is displayed on display screen 400 of user computing device 111c1 with instructions (e.g., message 412m) for treating, with the manufactured product (manufactured product 424r (e.g., shaving gel)) at least one feature (e.g., 120% pressure applied at pixel 202ap1) identifiable in the pixel data (e.g., pixel data 202ap) comprising the at least the portion of the shaving razor (e.g., pixel 202ap2) applied to the user's skin.

As shown in FIG. 4, user interface 402 recommends a product (e.g., manufactured product 424r (e.g., shaving gel)) based on the user-specific electronic recommendation 412. In the example of FIG. 4, the output or analysis of image(s) (e.g. image 202a) of pressure model (e.g., pressure model 108), e.g., user-specific electronic recommendation 412 and/or its related values (e.g., 120% pressure applied) or related pixel data (e.g., 202ap1 and/or 202ap2), may be used to generate or identify recommendations for corresponding product(s). Such recommendations may include products such as shaving gel, new shaving razor(s), shaving blade(s), a moisturizing treatment, or the like to address the user-specific issue as detected within the pixel data by the pressure model (e.g., pressure model 108).

In the example of FIG. 4, user interface 402 renders or provides a recommended product (e.g., manufactured product 424r) as determined by pressure model (e.g., pressure model 108) and its related image analysis of image 202a and its pixel data and various features. In the example of FIG. 4, this is indicated and annotated (424p) on user interface 402.

User interface 402 may further include a selectable UI button 424s to allow the user (e.g., the user of image 202a) to select for purchase or shipment the corresponding product (e.g., manufactured product 424r). In some embodiments, selection of selectable UI button 424s a may cause the recommended product(s) to be shipped to the user (e.g., individual 501) and/or may notify a third party that the individual is interested in the product(s). For example, either user computing device 111c1 and/or imaging server(s) 102 may initiate, based on user-specific electronic recommendation 412, the manufactured product 424r (e.g., shaving gel) for shipment to the user. In such embodiments, the product may be packaged and shipped to the user.

In various embodiments, graphical representation (e.g., image 202a), with graphical annotations (e.g., area of pixel data 202ap), textual annotations (e.g., text 202at), user-specific electronic recommendation 412 may be transmitted, via the computer network (e.g., from an imaging server 102 and/or one or more processors) to user computing device 111c1, for rendering on display screen 400. In other embodiments, no transmission to the imaging server of the user's specific image occurs, where the user-specific recommendation (and/or product specific recommendation) may instead be generated locally, by the pressure model (e.g., pressure model 108) executing and/or implemented on the user's mobile device (e.g., user computing device 111c1) and rendered, by a processor of the mobile device, on display screen 400 of the mobile device (e.g., user computing device 111c1).

In some embodiments, any one or more of graphical representations (e.g., image 202a), with graphical annotations (e.g., area of pixel data 202ap), textual annotations (e.g., text 202at), user-specific electronic recommendation 412, and/or product recommendation 422 may be rendered (e.g., rendered locally on display screen 400) in real-time or near-real time during or after the user shaving stroke is taken. In embodiments where the image is analyzed by imaging server(s) 102, the image may be transmitted and analyzed in real-time or near real-time by imaging server(s) 102.

In some embodiments, the user may provide a new image that may be transmitted to imaging server(s) 102 for updating, retraining, or reanalyzing by pressure model 108. In other embodiments, a new image that may be locally received on computing device 111c1 and analyzed, by pressure model 108, on the computing device 111c1.

In addition, as shown in the example of FIG. 4, the user may select selectable button 412i to for reanalyzing (e.g., either locally at computing device 111c1 or remotely at imaging server(s) 102) a new image. Selectable button 412i may cause user interface 402 to prompt the user to attach for analyzing a new image. Imaging server(s) 102 and/or a user computing device such as user computing device 111c1 may receive a new image of the user when shaving with the shaving razor. The new image may be captured by the digital camera. The new image (e.g., just like image 202a) may comprise pixel data of at least a portion of the shaving razor applied to the user's skin. The pressure model (e.g., pressure model 108), executing on the memory of the computing device (e.g., imaging server(s) 102), may analyze the new image captured by the digital camera to determine a new user-specific pressure being applied to the user's skin by the shaving razor when a new user shaving stroke is taken. The computing device (e.g., imaging server(s) 102) may generate, based on the new user-specific pressure, a new user-specific electronic recommendation or comment regarding at least one feature identifiable within the pixel data of the new image. For example the new user-specific electronic recommendation may include a new graphical representation including graphics and/or text (e.g., showing a new user-specific pressure value, e.g., 80%). The new user-specific electronic recommendation may include additional recommendations, e.g., that the user has overcorrected by applying too little pressure (e.g., at 80% of recommended pressure) as detected with the pixel data of the new image. A comment may include that the user has corrected the at least one feature identifiable within the pixel data (e.g., the user-specific pressure is now correct between 95% and 105%).

In some embodiments, a delta pressure value may be generated, by the one or more processors (e.g., a processor of imaging server(s) 102 and/or user computing device such as user computing device 111c1) based on a comparison between the new user-specific pressure and the user-specific pressure. In such embodiments, the new user-specific recommendation or comment may be further based on the delta pressure value. The delta pressure value, a representation of the delta pressure value (e.g., a graph or other graphical depiction), or a comment (e.g., text) based on the delta pressure value, may be rendered on the display screen of the user computing device (e.g., user computing device 111c1) to illustrate or describe the difference (delta) between the new user-specific pressure and the user-specific pressure as previously determined.

In various embodiments, the new user-specific recommendation or comment may be transmitted via the computer network, from server(s) 102, to the user computing device of the user for rendering on the display screen of the user computing device.

In other embodiments, no transmission to the imaging server of the user's new image occurs, where the new user-specific recommendation (and/or product specific recommendation) may instead be generated locally, by the pressure model (e.g., pressure model 108) executing and/or implemented on the user's mobile device (e.g., user computing device 111c1) and rendered, by a processor of the mobile device, on a display screen of the mobile device (e.g., user computing device 111c1).

ASPECTS OF THE DISCLOSURE

The following aspects are provided as examples in accordance with the disclosure herein and are not intended to limit the scope of the disclosure.

1. A digital imaging method of analyzing pixel data of an image of a shaving stroke for determining pressure being applied to a user's skin, the digital imaging method comprising the steps of: (a) aggregating, at one or more processors communicatively coupled to one or more memories, a plurality of training images of a plurality of individuals, each of the training images comprising pixel data of a respective individual when shaving with a shaving razor; (b) training, by the one or more processors with the pixel data of the plurality of training images, a pressure model operable to determine pressure being applied to the respective individual's skin by a shaving razor when a shaving stroke is taken; (c) receiving, at the one or more processors, at least one image of a user when shaving with the shaving razor, the at least one image captured by a digital camera, and the at least one image comprising pixel data of at least a portion of the shaving razor applied to the user's skin; (d) analyzing, by the pressure model executing on the one or more processors, the at least one image captured by the digital camera to determine a user-specific pressure being applied to the user's skin by the shaving razor when a user shaving stroke is taken; (e) generating, by the one or more processors based on the user-specific pressure, at least one user-specific electronic recommendation designed to address at least one feature identifiable within the pixel data comprising the at least the portion of the shaving razor applied to the user's skin; and (f) rendering, on a display screen of a user computing device, the at least one user-specific recommendation.

2. The digital imaging method of aspect 1, wherein the at least one user-specific electronic recommendation is displayed on the display screen of the user computing device with a graphical representation of the user's skin as annotated with one or more graphics or textual renderings corresponding to the user-specific pressure.

3. The digital imaging method of any one of aspects 1-2, wherein the at least one user-specific electronic recommendation is rendered in real-time or near-real time, during, or after the user shaving stroke is taken.

4. The digital imaging method of any one of aspects 1-3, wherein the at least one user-specific electronic recommendation comprises a product recommendation for a manufactured product.

5. The digital imaging method of aspect 4, wherein the at least one user-specific electronic recommendation is displayed on the display screen of the user computing device with instructions for treating, with the manufactured product, the at least one feature identifiable in the pixel data comprising the at least the portion of the shaving razor applied to the user's skin.

6. The digital imaging method of aspect 4, further comprising the steps of: initiating, based on the product recommendation, the manufactured product for shipment to the user.

7. The digital imaging method of aspect 4, further comprising the steps of: generating, by the one or more processors, a modified image based on the at least one image, the modified image depicting how the user's skin is predicted to appear after treating the at least one feature with the manufactured product; and rendering, on the display screen of the user computing device, the modified image.

8. The digital imaging method of any one of aspects 1-7, wherein the at least one user-specific electronic recommendation is displayed on the display screen of the user computing device with instructions for treating, with the shaving razor, the at least one feature identifiable in the pixel data comprising the at least the portion of the shaving razor applied to the user's skin.

9. The digital imaging method of any one of aspects 1-8, wherein the pressure model is an artificial intelligence (AI) based model trained with at least one AI algorithm.

10. The digital imaging method of any one of aspects 1-9, wherein the pressure model is further trained, by the one or more processors with the pixel data of the plurality of training images, to output one or more location identifiers indicating one or more corresponding body area locations of respective individuals, and wherein the pressure model, executing on the one or more processors and analyzing the at least one image of the user, determines a location identifier indicating a body area location of the user's body or body area.

11. The digital method of aspect 10, wherein the body area location comprises the user's cheek, the user's neck, the user's head, the user's groin, the user's underarm, the user's chest, the user's back, the user's leg, the user's arm, or the user's bikini area.

12. The digital method of any one of aspects 1-11, wherein training, by the one or more processors with the pixel data of the plurality of training images, the pressure model comprises training the pressure model to detect an amount of depression of the user's skin to determine the user-specific pressure being applied to the user's skin by the shaving razor when the shaving stroke is taken.

13. The digital method of any one of aspects 1-12, wherein training, by the one or more processors with the pixel data of the plurality of training images, the pressure model comprises training the pressure model to detect an angle of a razor cartridge with respect to a razor handle of the shaving razor to determine the user-specific pressure being applied to the user's skin by the shaving razor when the shaving stroke is taken.

14. The digital method of any one of aspects 1-13, wherein training, by the one or more processors with the pixel data of the plurality of training images, the pressure model comprises training the pressure model to detect an amount of depression of the user's skin in combination with an angle of a razor cartridge with respect to a razor handle of the shaving razor to determine the user-specific pressure being applied the a user's skin by the shaving razor when the shaving stroke is taken.

15. The digital method of any one of aspects 1-14, wherein training, by the one or more processors with the pixel data of the plurality of training images, the pressure model comprises training the pressure model to detect an amount of depression of the user's skin in combination with a direction in which a razor handle of the shaving razor is oriented relative to a body area of the user to determine the user-specific pressure being applied the a user's skin by the shaving razor when the shaving stroke is taken.

16. The digital method of any one of aspects 1-15, wherein training, by the one or more processors with the pixel data of the plurality of training images, the pressure model comprises training the pressure model to detect an amount of depression of the user's skin in combination with a hand grip pattern of the user on a razor handle of the shaving razor to determine the user-specific pressure being applied the a user's skin by the shaving razor when the shaving stroke is taken.

17. The digital method of any one of aspects 1-16, further comprising: receiving, at the one or more processors, a new image of the user when shaving with the shaving razor, the new image captured by the digital camera, and the new image comprising pixel data of at least a portion of the shaving razor applied to the user's skin; analyzing, by the pressure model executing on the one or more processors, the new image captured by the digital camera to determine a new user-specific pressure being applied to the user's skin by the shaving razor when a new user shaving stroke is taken; generating, based on the new user-specific pressure, a new user-specific electronic recommendation or comment regarding at least one feature identifiable within the pixel data of the new image; and rendering, on a display screen of a user computing device of the user, the new user-specific recommendation or comment.

18. The digital imaging method of claim 17, wherein a delta pressure value is generated based on a comparison between the new user-specific pressure and the user-specific pressure, wherein the new user-specific recommendation or comment is further based on the delta pressure value, and wherein the delta pressure value, a representation of the delta pressure value, or a comment based on the delta pressure value, is rendered on the display screen of the user computing device.

19. The digital method of any one of aspects 1-18, wherein the one or more processors comprises at least one of a server or a cloud-based computing platform, and the server or the cloud-based computing platform receives the plurality of training images of the plurality of individuals via a computer network, and wherein the server or the cloud-based computing platform trains the pressure model with the pixel data of the plurality of training images.

20. The digital method of aspect 19, wherein the server or a cloud-based computing platform receives the at least one image comprising the pixel data of at the least a portion of the shaving razor applied to the user's skin, and wherein the server or a cloud-based computing platform executes the pressure model and generates, based on output of the pressure model, the user-specific recommendation and transmits, via the computer network, the user-specific recommendation to the user computing device for rendering on the display screen of the user computing device.

21. The digital method of any one of aspects 1-20, wherein the user computing device comprises at least one of a mobile device, a tablet, a handheld device, a desktop device, a home assistant device, or a personal assistant device.

22. The digital method of any one of aspects 1-21, wherein the user computing device receives the at least one image comprising the pixel data of the at least a portion of the shaving razor applied to the user's skin, and wherein the user computing device executes the pressure model and generates, based on output of the pressure model, the user-specific recommendation, and renders the user-specific recommendation on the display screen of the user computing device.

23. The digital method of any one of aspects 1-22, wherein the at least one image comprises a plurality of images.

24. The digital method of any one of aspects 23, wherein the plurality of images are collected using a digital video camera.

25. The digital method of any one of aspects 1-24, wherein the shaving razor is a wet razor, a dry shaver, or an electric razor.

26. A digital imaging system configured to analyze pixel data of an image of a shaving stroke for determining pressure being applied to a user's skin, the digital imaging system comprising: an imaging server comprising a server processor and a server memory; an imaging application (app) configured to execute on a user computing device comprising a device processor and a device memory, the imaging app communicatively coupled to the imaging server; and a pressure model trained with pixel data of a plurality of training images of individuals and operable to determine pressure being applied to a respective individual's skin by a shaving razor when a shaving stroke is taken, wherein the pressure model is configured to execute on the server processor or the device processor to cause the server processor or the device processor to: receive at least one image of a user when shaving with the shaving razor, the at least one image captured by a digital camera, and the at least one image comprising pixel data of at least a portion of the shaving razor applied to the user's skin, analyze, by the pressure model, the at least one image captured by the digital camera to determine a user-specific pressure being applied to the user's skin by the shaving razor when a user shaving stroke is taken, generate, based on the user-specific pressure, at least one user-specific electronic recommendation designed to address at least one feature identifiable within the pixel data comprising the at least the portion of the shaving razor applied to the user's skin, and render, on a display screen of the user computing device of the user, the at least one user-specific recommendation.

27. A tangible, non-transitory computer-readable medium storing instructions for analyzing pixel data of an image of a shaving stroke for determining pressure being applied to a user's skin, that when executed by one or more processors cause the one or more processors to: (a) aggregate, at one or more processors communicatively coupled to one or more memories, a plurality of training images of a plurality of individuals, each of the training images comprising pixel data of a respective individual when shaving with a shaving razor; (b) train, by the one or more processors with the pixel data of the plurality of training images, a pressure model operable to determine pressure being applied to the respective individual's skin by a shaving razor when a shaving stroke is taken; (c) receive, at the one or more processors, at least one image of a user when shaving with the shaving razor, the at least one image captured by a digital camera, and the at least one image comprising pixel data of at least a portion of the shaving razor applied to the user's skin; (d) analyze, by the pressure model executing on the one or more processors, the at least one image captured by the digital camera to determine a user-specific pressure being applied to the user's skin by the shaving razor when a user shaving stroke is taken; (e) generate, by the one or more processors based on the user-specific pressure, at least one user-specific electronic recommendation designed to address at least one feature identifiable within the pixel data comprising the at least the portion of the shaving razor applied to the user's skin; and (f) render, on a display screen of a user computing device, the at least one user-specific recommendation.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital imaging method of analyzing pixel data of an image of a shaving stroke for determining pressure being applied to a user's skin, the digital imaging method comprising the steps of:
    a. aggregating, at one or more processors communicatively coupled to one or more memories, a plurality of training images of a plurality of individuals, each of the training images comprising pixel data of a respective individual when shaving with a shaving razor;
    b. training, by the one or more processors with the pixel data of the plurality of training images, a pressure model operable to determine pressure being applied to the respective individual's skin by a shaving razor when a shaving stroke is taken;

c. receiving, at the one or more processors, at least one image of a user when shaving with the shaving razor, the at least one image captured by a digital camera, and the at least one image comprising pixel data of at least a portion of the shaving razor applied to the user's skin;

d. analyzing, by the pressure model executing on the one or more processors, the at least one image captured by the digital camera to determine a user-specific pressure being applied to the user's skin by the shaving razor when a user shaving stroke is taken;

e. generating, by the one or more processors based on the user-specific pressure, at least one user-specific electronic recommendation designed to address at least one feature identifiable within the pixel data comprising the at least the portion of the shaving razor applied to the user's skin;

f. rendering, on a display screen of a user computing device, the at least one user-specific recommendations;

g. receiving, at the one or more processors, a new image of the user when shaving with the shaving razor, the new image captured by the digital camera, and the new image comprising pixel data of at least a portion of the shaving razor applied to the user's skin;

h. analyzing, by the pressure model executing on the one or more processors, the new image captured by the digital camera to determine a new user-specific pressure being applied to the user's skin by the shaving razor when a new user shaving stroke is taken;

i. generating, based on the new user-specific pressure, a new user-specific electronic recommendation or comment regarding at least one feature identifiable within the pixel data of the new image; and j. rendering, on a display screen of a user computing device of the user, the new user-specific recommendation or comment, wherein a delta pressure value is generated based on a comparison between the new user-specific pressure and the user-specific pressure, wherein the new user-specific recommendation or comment is further based on the delta pressure value, and wherein the delta pressure value, a representation of the delta pressure value, or a comment based on the delta pressure value, is rendered on the display screen of the user computing device.

2. The digital imaging method of claim 1, wherein the at least one user-specific electronic recommendation is displayed on the display screen of the user computing device with a graphical representation of the user's skin as annotated with one or more graphics or textual renderings corresponding to the user-specific pressure.

3. The digital imaging method of claim 1, wherein the at least one user-specific electronic recommendation is rendered in real-time or near-real time, during, or after the user shaving stroke is taken.

4. The digital imaging method of claim 1, wherein the at least one user-specific electronic recommendation comprises a product recommendation for a manufactured product.

5. The digital imaging method of claim 4, wherein the at least one user-specific electronic recommendation is displayed on the display screen of the user computing device with instructions for treating, with the manufactured product, the at least one feature identifiable in the pixel data comprising the at least the portion of the shaving razor applied to the user's skin.

6. The digital imaging method of claim 4, further comprising the steps of:
initiating, based on the product recommendation, the manufactured product for shipment to the user.

7. The digital imaging method of claim 4, further comprising the steps of:
generating, by the one or more processors, a modified image based on the at least one image, the modified image depicting how the user's skin is predicted to appear after treating the at least one feature with the manufactured product; and
rendering, on the display screen of the user computing device, the modified image.

8. The digital imaging method of claim 1, wherein the at least one user-specific electronic recommendation is displayed on the display screen of the user computing device with instructions for treating, with the shaving razor, the at least one feature identifiable in the pixel data comprising the at least the portion of the shaving razor applied to the user's skin.

9. The digital imaging method of claim 1, wherein the pressure model is an artificial intelligence (AI) based model trained with at least one AI algorithm.

10. The digital imaging method of claim 1,
wherein the pressure model is further trained, by the one or more processors with the pixel data of the plurality of training images, to output one or more location identifiers indicating one or more corresponding body area locations of respective individuals, and
wherein the pressure model, executing on the one or more processors and analyzing the at least one image of the user, determines a location identifier indicating a body area location of the user's body or body area.

11. The digital method of claim 10, wherein the body area location comprises the user's cheek, the user's neck, the user's head, the user's groin, the user's underarm, the user's chest, the user's back, the user's leg, the user's arm, or the user's bikini area.

12. The digital method of claim 1, wherein training, by the one or more processors with the pixel data of the plurality of training images, the pressure model comprises training the pressure model to detect an amount of depression of the user's skin to determine the user-specific pressure being applied to the user's skin by the shaving razor when the shaving stroke is taken.

13. The digital method of claim 1, wherein training, by the one or more processors with the pixel data of the plurality of training images, the pressure model comprises training the pressure model to detect an angle of a razor cartridge with respect to a razor handle of the shaving razor to determine the user-specific pressure being applied to the user's skin by the shaving razor when the shaving stroke is taken.

14. The digital method of claim 1, wherein training, by the one or more processors with the pixel data of the plurality of training images, the pressure model comprises training the pressure model to detect an amount of depression of the user's skin in combination with an angle of a razor cartridge with respect to a razor handle of the shaving razor to determine the user-specific pressure being applied the a user's skin by the shaving razor when the shaving stroke is taken.

15. The digital method of claim 1, wherein training, by the one or more processors with the pixel data of the plurality of training images, the pressure model comprises training the pressure model to detect an amount of depression of the user's skin in combination with a direction in which a razor handle of the shaving razor is oriented relative to a body area of the user to determine the user-specific pressure being applied the a user's skin by the shaving razor when the shaving stroke is taken.

16. The digital method of claim 1, wherein training, by the one or more processors with the pixel data of the plurality of training images, the pressure model comprises training the pressure model to detect an amount of depression of the user's skin in combination with a hand grip pattern of the user on a razor handle of the shaving razor to determine the user-specific pressure being applied the a user's skin by the shaving razor when the shaving stroke is taken.

17. The digital method of claim 1, wherein the one or more processors comprises at least one of a server or a cloud-based computing platform, and the server or the cloud-based computing platform receives the plurality of training images of the plurality of individuals via a computer network, and wherein the server or the cloud-based computing platform trains the pressure model with the pixel data of the plurality of training images.

18. The digital method of claim 17, wherein the server or a cloud-based computing platform receives the at least one image comprising the pixel data of at the least a portion of the shaving razor applied to the user's skin, and wherein the server or a cloud-based computing platform executes the pressure model and generates, based on output of the pressure model, the user-specific recommendation and transmits, via the computer network, the user-specific recommendation to the user computing device for rendering on the display screen of the user computing device.

19. The digital method of claim 1, wherein the user computing device comprises at least one of a mobile device, a tablet, a handheld device, a desktop device, a home assistant device, a personal assistant device, or a retail computing device.

20. The digital method of claim 1, wherein the user computing device receives the at least one image comprising the pixel data of the at least a portion of the shaving razor applied to the user's skin, and wherein the user computing device executes the pressure model and generates, based on output of the pressure model, the user-specific recommendation, and renders the user-specific recommendation on the display screen of the user computing device.

21. The digital method of claim 1, wherein the at least one image comprises a plurality of images.

22. The digital method of claim 21, wherein the plurality of images are collected using a digital video camera.

23. The digital method of claim 1, wherein the shaving razor is a wet razor, a dry shaver, or an electric razor.

24. A digital imaging system configured to analyze pixel data of an image of a shaving stroke for determining pressure being applied to a user's skin, the digital imaging system comprising:
an imaging server comprising a server processor and a server memory;
an imaging application (app) configured to execute on a user computing device comprising a device processor and a device memory, the imaging app communicatively coupled to the imaging server; and
a pressure model trained with pixel data of a plurality of training images of individuals and operable to determine pressure being applied to a respective individual's skin by a shaving razor when a shaving stroke is taken, wherein the pressure model is configured to execute on the server processor or the device processor to cause the server processor or the device processor to:
receive at least one image of a user when shaving with the shaving razor, the at least one image captured by a digital camera, and the at least one image comprising pixel data of at least a portion of the shaving razor applied to the user's skin,
analyze, by the pressure model, the at least one image captured by the digital camera to determine a user-specific pressure being applied to the user's skin by the shaving razor when a user shaving stroke is taken,
generate, based on the user-specific pressure, at least one user-specific electronic recommendation designed to address at least one feature identifiable within the pixel data comprising the at least the portion of the shaving razor applied to the user's skin,
render, on a display screen of the user computing device of the user, the at least one user-specific recommendations;
receive, at the one or more processors, a new image of the user when shaving with the shaving razor, the new image captured by the digital camera, and the new image comprising pixel data of at least a portion of the shaving razor applied to the user's skin;
analyze, by the pressure model executing on the one or more processors, the new image captured by the digital camera to determine a new user-specific pressure being applied to the user's skin by the shaving razor when a new user shaving stroke is taken;
generate, based on the new user-specific pressure, a new user-specific electronic recommendation or comment regarding at least one feature identifiable within the pixel data of the new image; and
render, on a display screen of a user computing device of the user, the new user-specific recommendation or comment,
wherein a delta pressure value is generated based on a comparison between the new user-specific pressure and the user-specific pressure, wherein the new user-specific recommendation or comment is further based on the delta pressure value, and wherein the delta pressure value, a representation of the delta pressure value, or a comment based on the delta pressure value, is rendered on the display screen of the user computing device.

25. A tangible, non-transitory computer-readable medium storing instructions for analyzing pixel data of an image of a shaving stroke for determining pressure being applied to a user's skin, that when executed by one or more processors cause the one or more processors to:
a. aggregate, at one or more processors communicatively coupled to one or more memories, a plurality of training images of a plurality of individuals, each of the training images comprising pixel data of a respective individual when shaving with a shaving razor;
b. train, by the one or more processors with the pixel data of the plurality of training images, a pressure model operable to determine pressure being applied to the respective individual's skin by a shaving razor when a shaving stroke is taken;
c. receive, at the one or more processors, at least one image of a user when shaving with the shaving razor, the at least one image captured by a digital camera, and the at least one image comprising pixel data of at least a portion of the shaving razor applied to the user's skin;
d. analyze, by the pressure model executing on the one or more processors, the at least one image captured by the digital camera to determine a user-specific pressure being applied to the user's skin by the shaving razor when a user shaving stroke is taken;
e. generate, by the one or more processors based on the user-specific pressure, at least one user-specific electronic recommendation designed to address at least one feature identifiable within the pixel data comprising the at least the portion of the shaving razor applied to the user's skin;
f. render, on a display screen of a user computing device, the at least one user-specific recommendations;
g. receive, at the one or more processors, a new image of the user when shaving with the shaving razor, the new image captured by the digital camera, and the new image comprising pixel data of at least a portion of the shaving razor applied to the user's skin;
h. analyze, by the pressure model executing on the one or more processors, the new image captured by the digital camera to determine a new user-specific pressure being applied to the user's skin by the shaving razor when a new user shaving stroke is taken;
i. generate, based on the new user-specific pressure, a new user-specific electronic recommendation or comment regarding at least one feature identifiable within the pixel data of the new image; and
j. render, on a display screen of a user computing device of the user, the new user-specific recommendation or comment,
wherein a delta pressure value is generated based on a comparison between the new user-specific pressure and the user-specific pressure, wherein the new user-specific recommendation or comment is further based on the delta pressure value, and wherein the delta pressure value, a representation of the delta pressure value, or a comment based on the delta pressure value, is rendered on the display screen of the user computing device.

* * * * *